(12) United States Patent
Berger et al.

(10) Patent No.: US 6,280,755 B1
(45) Date of Patent: Aug. 28, 2001

(54) FATTY ACID UNINTERRUPTED BY A METHYLENE AS ANTI-INFLAMMATORY AGENTS IN SUPERFICIAL TISSUES OF MAMMALS

(75) Inventors: Alvin Berger, St. Sulpice (CH); Andre Jomard, Saint Vallier de Thiey (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/555,017
(22) PCT Filed: Dec. 1, 1998
(86) PCT No.: PCT/FR98/02584
§ 371 Date: Sep. 5, 2000
§ 102(e) Date: Sep. 5, 2000
(87) PCT Pub. No.: WO99/27924
PCT Pub. Date: Jun. 10, 1999

(30) Foreign Application Priority Data

Dec. 1, 1997 (FR) .................................................. 97 203752

(51) Int. Cl.[7] .............................. A61K 7/00; A61K 9/54; A61K 9/127; A61K 47/00
(52) U.S. Cl. .................... 424/401; 424/458; 424/450; 514/943; 514/844; 514/887; 514/863; 514/861; 514/864; 514/859; 514/858
(58) Field of Search .................................. 424/401, 458, 424/400, 450; 514/943, 844, 887, 863, 861, 864, 859, 858

(56) References Cited

U.S. PATENT DOCUMENTS 5,472,705    12/1995    Bruzzese et al. .

FOREIGN PATENT DOCUMENTS 2 756 465    6/1998    (FR) .
95 17897    7/1995    (WO) .

*Primary Examiner*—Thurman K. Page
*Assistant Examiner*—Rachel M. Bennett
(74) *Attorney, Agent, or Firm*—Burns, Doane, Swecker & Mathis, L.L.P.

(57) ABSTRACT

The invention concerns fatty acids uninterrupted by a methylene group as anti-inflammatory agents in superficial tissues of mammals, more particularly a pharmaceutical or cosmetic topical composition comprising, as an active ingredient, at least one fatty acid uninterrupted by a methylene group corresponding to formula (I),

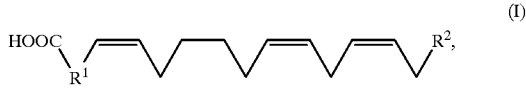

(I)

an salt or ester thereof, wherein $R^1$ is a $C_1$–$C_5$ alkyl group and $R^2$ is a $C_2$–$C_6$ alkyl group. Preferably, the fatty acid uninterrupted by a methylene group is 20:3(5,11,14). The fatty acid uninterrupted by a methylene group is also used for preparing a composition for modulating the metabolism of lipids in the superficial tissue of mammals.

22 Claims, No Drawings

FATTY ACID UNINTERRUPTED BY A METHYLENE AS ANTI-INFLAMMATORY AGENTS IN SUPERFICIAL TISSUES OF MAMMALS

This application is a 371 of PCT/FR98/02584 filed Dec. 1, 1998.

The present invention relates to the new use of a non-methylene interrupted fatty acid in the prevention and/or the treatment of inflammation in superficial mammalian tissues.

BACKGROUND OF THE INVENTION

The use of fatty acids for preventing and/or treating inflammation in superficial tissues has been described in the literature.

For example, EP 5 472 705 (Prospa B. V.) discloses new pharmaceutical compositions for topical use containing esters of ω-3 polyunsaturated acids in a high concentration and intended for treating psoriasis, phlebitis and related pathologies.

EP 582 239 (Rhône-Poulenc Rorer) discloses topical pharmaceutical and cosmetic compositions containing linoleic acid or derivatives thereof as active ingredients, and a carrier for transporting the active ingredient into the skin. These compositions are used for the prophylaxis and treatment of impure skin, e.g. skin affected by pimples, pustules, urticaria or comedones, of acne and of acne-associated skin disorders.

Furthermore, EP 5 312 834 (Woobang Land Co.) discloses a pharmaceutical composition for treating acne comprising eicosapentaenoic acid and (α-linolenic acid, in a weight ratio of 1:0.1 to 20:0.1 of eicosapentaenoic acid to α-linolenic acid respectively. These fatty acids may be extracted from natural substances such as fish oil and/or perilla oil, for example.

The term non-methylene-interrupted fatty acid, the acronym for which is NMIFA, refers to a fatty acid with a series of double bonds in which at least one adjacent pair of double bonds is separated by at least two carbon atoms, i.e., by a group other than a single methylene group. NMIFAs have been the subject of only a few studies with the aim of developing an understanding of their incorporation into mammalian tissues and their potential role in the treatment of certain diseases.

For example, JP 61 058 536 (Nippon Oil) discloses a method for purifying pine nut oil containing at least 10% by weight of 5,9,12-cis-octadecatrienoic acid which exhibits a curative effect against arterial hypertension. WO 96 05 164 (Broadben Nominees Pty) discloses an anti-inflammatory preparation comprising a purified active fraction, for example 5,11,14,17-eicosatetraenoic acid, isolated from a lipid extract of *Perna canalicullus* or *Mytilus edulis*.

WO 95 17 987 (The Regents of the University of California) shows that broad class of NMIFAs, including 5,11,14-eicosatrienoic acid, may be used in an effective amount for suppressing autoimmune diseases in general, for example rheumatoid arthritis, lupus erythmatosis, multiple sclerosis, myasthenia gravis, and about 30 other diseases currently known.

Incorporation of dietary 5,11,14-eicosatrienoate into various mouse phospolipid classes and tissues has been studied. Results show that feeding the mice 5,11,14-eicosatrienoate resulted in lower levels of 20:4n-6 in the hepatic phosphatidylinositol pool. Because leukotrienes and prostaglandins cannot be formed from 5,11,14-eicosatrienoate due to the lack of an internal Δ8 double bond, and because 20:4n-6 was dramatically reduced in some phosphatidylinositol pools, it was expected that dietary intake of 5,11,14-eicosatrienate may alter eicosanoid metabolism, thus reducing potential inflammation in the hepatic system (Biochemica et Biophysica Acta, 1085, 371–376, 1991; J. Nutr. Biochem., 4, 409–420,1993).

So far, the following class of NMIFAs, especially 5,11, 14-eicosatrienoic acid has not been reported as being capable of being incorporated into the lipid fraction of superficial mammalian tissues. Neither has an anti-inflammatory effect in superficial mammalian tissues been expected.

SUMMARY OF THE INVENTION

Accordingly, it has been found that the NMIFAs having the following formula, wherein the NMIFA is an acid, a salt or an ester, and $R^1$ is a $C_1$–$C_5$ alkyl group and $R_2$ is a $C_2$–$C_6$ alkyl group, may be advantageously used for the preparation of a composition intended to modulate the metabolism of lipids in superficial mammalian tissues.

Particularly preferred NMIFAs are those in which $R^1$ is a $C_3$ alkyl group and $R^2$ is a $C_2$–$C_6$ alkyl group, or in which $R^2$ is a $C_4$ alkyl group and $R^1$ is a $C_1$–$C_5$ alkyl group. The most preferred is that in which $R^1$ is an n-propyl group and $R^2$ is an n-butyl group (5,11,14-eicosatrienoic acid, also called 20:3(5,11,14)).

The NMIFAs of the invention may also be used in this context for the preparation of a composition intended to treat or prevent inflammations is superficial mammalian tissues by modulating the metabolism of the lipids. The invention also relates to topical pharmaceutical and cosmetic compositions comprising the NMIFAs of the invention as active ingredient. In a last aspect, the invention provides a pharmaceutical, food or cosmetic composition comprising a combination of fish oil and the NMIFAs of the invention.

The NMIFAs of the invention offer similar advantages as fish oils known to one skilled in the art. However, they provide the advantage of being less oxidizable than fish oil, since they have only two methylene interrupted bonds as compared to docosahexaenoic acid contained in fish oil having 6 methylene interrupted bonds. In addition the NMIFAs of the invention are not a substrate for prostaglandin and leukotriene production, whereas prostaglandin and leukotriene can be formed from the fatty acids found in fish oil, such as 20:5n-3 and 22:6n-3. A further advantage over fish oil preparation is the lack of "fishy" odour.

DETAILED DESCRIPTION OF THE INVENTION

"Modulation of the metabolism of lipids" is understood as meaning more particularly catabolism of the lipid mediators associated with inflammation, differentiation, proliferation and/or barrier function of superficial tissues.

Furthermore, inflammation of superficial tissues must be understood as the physiological phenomenon involving the production of pro-inflammatory cytokines, such as cachectin α (TNFα), by the cells of superficial tissues, for example the keratinocytes and the epithelial cells of the cornea, and the cells of the immune system which are contained in these tissues (lymphocytes, Langerhans' cells and the like). The inflammation may result, for example, from an infection, an allergy, a wound and an exposure to radiation and/or irritating agents and/or sensitizing agents.

The fatty acid which is the subject of this invention is a polyunsaturated fatty acid which is linear and monocarboxylic, with all double bonds being cis-double bonds. Several types of nomenclature are used in this specification, and these are as follows.

a) Nomenclature for individual compounds indicating number of carbon atoms and number and position of double bonds, a typical example being "20:4(5,8,11,14)" for arachidonic acid: the number preceding the colon is the total number of carbon atoms, the number immediately following the colon is the number of double bonds, and the numbers in parentheses are the positions of the double bonds, starting from the end of the chain bearing the carboxylic acid group. In all compounds represented in this manner, except where otherwise indicated, all double bonds are cis.

b) Nomenclature for classes of compounds indicating the location of the double bond closest to the methyl end group, a typical example being "n-3" or "n-6": the number following the dash denotes the position of the double bond closest to the methyl end of the molecule, counting from the methyl end. Thus, arachidonic acid is in the n-6 class, as is 5,11,14-eicosatrienoic acid (20:3(5,11,14,)), whereas 5,8,11,14,17-eicosapentaenoic acid (20:5(5,8,11,14,17)) is in the n-3 class. This nomenclature is equivalent to "ω" nomenclature in the literature, "ω" and "n" being interchangeable.

Some of the NMIFAs of the invention are naturally occurring substances. Others may be synthesized according to well known published methodology (see for example Evans et al., Chem. Phys. Lipids, 38, 327–342, 1995).

For example, 20:3(5,11,14) is a naturally occurring substance which generally occurs as one fatty acid in a mixture of fatty acids. This NMIFA is found in a wide variety of plants as minor or major fraction of the total fatty acid composition. Both the extraction of the mixture of fatty acid from their natural sources and the extraction of the 20:3(5,11,14) from the resulting fatty acids can be achieved by conventional extraction and purification methods well known among those skilled in the art.

The natural sources of fatty acids containing 20:3(5,11,14) are primarily plant seeds, and prominent among these are conifers and ornamental shrubs. The seed oils from these plants are similar to normal edible oils, containing largely oleic, linoleic and linolenic acids, but also containing useful amounts of NMIFAs. Table 1 lists examples of seeds whose lipid contents contain significant amounts of 20:3(5,11,14).

TABLE 1

| Source | % of 20:3 (5,11,14) among total fatty acids | Source | % of 20:3 (5,11,14) among total fatty acids |
| --- | --- | --- | --- |
| Juniperis virginiensis | 14.8 | Sciadopitys verticallata | 15 |
| Plarycladus orientalis | 3 | Caltha palustris | 23 |
| Juniperis chinesis | 12.3 | Calitrus rhombaidea | 14 |
| Torreya nucifera | 7 | Mortierella alpina* | 7 |
| Podocarpus nagi | 24 | Ephedra campylopoda | 22 |
| Anemone | 10 | Anemone | 6 |

TABLE 1-continued

| Source | % of 20:3 (5,11,14) among total fatty acids | Source | % of 20:3 (5,11,14) among total fatty acids |
| --- | --- | --- | --- |
| rivularis | | leveillei | |
| Cimaifuga racemosa | 6 | Erantis hyemalis | 6 |
| Gingko biloba | 2.2 | Pinus silvestris | 7 |

*see the Japanese patent JP5276964 (Suntory LTD)

Purification of 20:3(5,11,14) may be in particular achieved by (1) choosing a starting seed source high in total fat content and 20:3(5,11,14) content but not containing other contaminating trienes, in particular α-linolenic acid (18:3n-3) and γ-linolenic acid (18:3n-6) (Podocarpus nagi, Table 1, is such an example); (2) extracting the lipids with isopropanol and chloroform according to the method of Nichols (Biochim. Biophys Acta 70: 417, 1963); (3) conventional degumming and decolouring methods; (4) preparing methyl esters with 2% methanolic sulphuric acid according to the method of Christie (p. 52–53, in Lipid Analysis, Pergamon Press, Oxford, 1982); (5) eluting 20:3(5,11,14) methyl ester from a silver nitrate impregnated acid-washed Florisil column with a hexane:ether mixture ranging from 9:1 to 8:2 (volume/volume) according to Carroll, J. Am. Oil Chem. Soc. 40: 413, 1963; Wilner, Chem. Ind (Lond) October, 30: 1839, 1965; Merck ChromNews 4(1): 1995; Anderson, J. Lipid Res. 6: 577, 1965; and Teshima, Bull. Jap. Soc. Scien. Fish. 44: 927, 1978); (6) removing contaminating silver ions by the method of Akesson (Eur. J. Biochem. 9:463, 1969); and (7) optionally converting the methyl ester back to the free acid form by saponification in 1 M potassium hydroxide in 95% ethanol according to Christie (p. 51–52, in Lipid Analysis, Pergamon Press, Oxford, 1982).

In the context of the present invention, the NMIFAs of the invention may be used in acid, salt or ester form, for example in methyl ester, ethyl ester, mono-, di-, tri-glyceride or phospholipid ester form. The NMIFAs of the invention may be used in a purified form, or else in the form of a mixture of fatty acids present in an oil extracted from one of the plants described above, for example.

Administration of the NMIFAs may be achieved by methods known to one skilled in the art, to any kind of superficial mammalian tissues, that is to say to cells which make up the skin, the scalp, the eye, or the oral, buccal, nasal and vaginal mucosa, for example.

The NMIFAs may be used for the treatment or prophylaxis of diseases of the skin or of the scalp, in particular against inflammations associated with, for example, psoriasis, erythema (sunburn), eczema, seborrhoeic dermatitis, alopecia areata, mycosis, acne and other dermatoses.

A composition of the invention, intended for topical applications, may thus comprise an effective amount of the NMIFAs as active ingredient, and a carrier for transporting the active ingredient into superficial mammalian tissues.

The carrier may be any kind of carrier known to one skilled in the art for cosmetic or pharmaceutical formulations. Liposomes may thus be one of the carriers used in this context. These molecules include one or more types of diverse substances including nonpolar lipids, polar lipids, mono- and diglycerides, sulphatides, lysolecithin, phospholipids, saponin, bile acids and salts. Liposomes can exist in the form of emulsions and foams, micelles, insoluble monolayers, liquid crystals, phospholipid dispersions and lamellar layers. The NMIFAs can be incorporated in the liposome, optionally in conjunction with an appropriate ligand or mimetic agent which binds to specific cell receptors.

Liposomes are generally formed from standard vesicle forming lipids, which generally include neutral or negatively charged phospholipids and a sterol, such as cholesterol. The selection of lipids is generally guided by consideration of various factors, such as for example the desired liposome size and the need for stability of the liposomes in the bloodstream. Typically, the major lipid component in the liposomes is phosphatidylcholine. Partially hydrogenated egg phospatidylcholine is a typical example.

Liposomes typically contain about 5–15 mole per cent of negatively charged phospholipids, such as phospatidylglycerol, phospatidylserine or phospatidylinositol. Negatively charged phospholipids help prevent spontaneous aggregation of the liposomes and thus lower the incidence of aggregates formed from undersized liposomes. Membrane rigidifying agents, such as sphingomyelin or a saturated neutral phospholipid, at a concentration of at least about 50 mole per cent, and 5–15 mole per cent of monosialylganglioside, may also by included to provide increased circulation of the liposome preparation in the bloodstream.

Liposome suspensions may also include lipid-protective agents to protect the lipids from free-radical and lipid-peroxidative damage during storage. Examples of these agents are lipophilic free-radical scavengers such as α-tocopherol, and water-soluble iron-specific chelators such as ferrioxyamine.

Liposomes can be prepared by a variety of methods known among those skilled in the art. The liposomes can then be sized within a desired particle size range and a relatively narrow particle size distribution. A size range which permits the liposome suspension to be sterilized by filtration through a conventional filter, for example, is about 0.2–0.4 microns.

Formulations for administration will generally comprise a solution of the compound dissolved or suspended in an acceptable vehicle, the appropriate choices of which will readily occur to those skilled in the art. The formulations may further contain pharmaceutically acceptable auxiliary substances as required to approximate physiological conditions, such as pH adjusting and buffering agents, tonicity adjusting agents, and wetting agents. The formulations may also advantageously include antioxidants, preferably fat-soluble antioxidants, such as especially tocopherol, tocopherol acetate, butylated hydroxytoluene, butylated hydroxyanisole, ascorbyl palmitate and mixtures thereof.

The cosmetic or pharmaceutical composition may be applied directly to the superficial tissues such that the NMIFAs diffuse through the cells and are administered there. This composition can also be injected underneath the superficial tissues, for example by means of a subcutaneous injection. In both cases, the application is regarded as topical, that is to say it is applied directly onto or underneath the superficial tissues.

Application of the NMIFAs can also be extended to inflammations of the eye, more particularly of the cornea, and also of the mucosa, more particularly of the oral, nasal, buccal, anal and vaginal mucosa. Compositions administered orally may affect directly the buccal, oesophageal, gastric and intestinal mucosa, and/or may pass into the bloodstream and be carried directly, for example, to the cells of the skin, the eye or the mucosa.

This composition can also by applied into the nasal passages by means of a diffuser, a gel and/or a physiological liquid for conventional flushing of the nasal passages.

It should be pointed out that, depending on the galenical forms usually used for topical or oral application, that is to say depending on the dietary, cosmetic and/or pharmaceutical form, the amount of NMIFAs sufficient and necessary to observe an anti-inflammatory effect or an effect as a modulator of the metabolism of lipids may vary considerably. The invention thus relates to the use of the NMIFAs in an amount sufficient for treatment or prevention of inflammations and/or for modulations of the metabolism of lipids of the superficial tissues.

The NMIFAs will thus be administered to a human or an animal, for example, as a food material to treat oral mucosa. They may thus be used as replacement for the oils normally used in food formulations or recipes, or as part of a mixture of oils used in this manner. This composition can be, for example, a sauce, such as a salad sauce, a table oil, a mayonnaise, an ice cream, a confectionery composition or a filling paste or spreading paste. The compound can also be administered as part of a nutritional supplement, such as a tablet or as a capsule taken orally on a daily basis. Binders, matrices and other conventional adjuvants normally found in supplements of these types will generally be included here as well. Typical dosages for such methods may vary widely, but will most often fall within the range of about 2 mg per kg of body weight to about 2000 mg per kg, and more often within the range of about 5 to about 500 mg per kg.

The food composition may preferably comprise a carrier to transport the NMIFAs to the large intestine or other region of the gastrointestinal tract. The carrier may be a resistant starch incorporated at a level of 2 to 20% by weight. Incorporation can be achieved while drying together the food components, by freeze drying, for example. Incorporation can also be achieved by microencapsulation. A typical process for microencapsulation requires the preheating of a low melting point oil above its melting point (<40° C.), the NMIFAs are then added to the mixture, resistant starch is also added together with other ingredients and binding agents such as gelatin and gums, and the dispersion is sprayed into the head of a cooling tower to allow uniform particles to form with an average size typically in the range 20–200 microns. A preferred form of resistant starch is a high amylose starch, for example those disclosed in WO 94/03 049 and WO 94/14 342.

In the field of human and animal cosmetics, the invention also relates to the use of the NMIFAs for the preparation of a galenical form usually used for topical or oral hygiene application, and in particular in the form of oily, alcoholic or aqueous-alcoholic solutions, gels, water-in-oil or oil-in-water emulsions having the appearance of a cream or a gel, if necessary capable of foaming, in the form of an aerosol, or also in the form of vesicular dispersions comprising ionic and/or non-ionic lipids. These galenical forms are in all cases prepared by the usual methods in the cosmetic field under consideration. This composition can be, for example, in particular, a composition for cleansing, protecting, treating or caring for the scalp, for the face, for the neck, for the hands, or for the body (for example in the form of vanishing creams, night creams, make-up remover creams, suncreams or oils, oils for the body or the face, cleansing milks, make-up remover milks or body milks), a make-up composition (for example a foundation), an artificial tanning composition, a composition for bathing, a shampoo composition (treatment of the scalp) or a composition for buccal hygiene (mouthwash, toothpaste or chewing gum).

In the field of human or animal pharmacy, in particular dermatology, oto-rhinolaryngology, ophthalmology, gastro-enterology and gynaecology, this composition can be, for example, a capsule, a soft gelatin capsule, an emulsion, a pomade, a composition which can be injected underneath the skin, an ointment, a syrup, a diffuser, an eyewash, a shampoo or a mouthwash comprising the NMIFAs for treatment or prophylaxis of the skin, the eyes or the mucosa. The various possible galenical forms are in all cases prepared by the usual methods of the pharmaceutical field under consideration.

The present invention is described in more detail by the examples given below. It goes without saying, however, that these examples are given only by way of illustration of the subject matter of the invention, of which they constitute no limitation in any manner. The percentages are given by weight, unless indicated otherwise.

EXAMPLE 1
Metabolism of 20:3(5,11,14)

Determination of the profile of 5,11,14 in the human immortalized keratinocyte line DK2-NR (described in the patent PCT/EP96/05812) was achieved as follows.

Confluent cultures of DK2-NR are incubated for 4 days in NR-2 medium (Biofluids Inc. Rockville, Md., USA) with an increased $Ca^{2+}$-concentration ($CaCl_2$:1.5 mM). Then, the keratinocytes are incubated twice in 2 days (medium change with fatty acids after 2 days) in NR-2 containing 1 mg/ml bovine serum albumin (BSA, fatty acid free, Sigma Inc. St. Louis, USA) and 15 mM of 5,11,14-eicosatrienoic acid methyl ester (5,11,14-ester) and/or arachidonic acid methyl ester (20;4n-6-ester).

Furthermore, the cells are preincubated for two days with 15 mM 20:4n-6-ester (see table No 6–9) and subsequently for 2×2 days with 5,11,14-ester and with a mixture of 20:4n-6-ester and 5,11,14-ester.

At the end of the incubation time the cells are washed in HBSS (Hanks Balanced Salt Solution) (Gibco, Life Technologies) containing 0.1% BSA and twice in HBSS. The cells are harvested by scraping (cell scraper, Costar Inc.) the cells from the culture dishes. The cells are centrifuged in 1 ml HBSS (1000 rpm). The cell extraction is carried out in a mixture of hexane and isopropanol (2:1 v/v) containing 2,6-di-tert-butyl-p-cresol. The phospholipids are separated by chromatography (silica gel 60) with the eluent chloroform/acetone (96:4 v/v). The fatty acid fraction of the phospholipids is then esterified by heating (100° C.) in a solution containing 10% $BF_3$-methanol (Supelco, Bellefonte, Pa., USA). The methyl esters are separated. The fatty acids are quantified according to internal standards.

The results listed in table 2 below show that 5,11,14-eicosatrienoic acid is integrated into the total lipids (3.34%).

TABLE 2

| | Treatment with fatty acids | | Phospholipid fatty acids in cells | | | |
|---|---|---|---|---|---|---|
| N° | Day 0 | Day 2 | Day 4 | 5,11, 14 % | 20:3n-6 % | 20:4n-6 % | 20:5n-3 % |
| 1 | — | Ethanol | Ethanol | 0.00 | 0.11 | 0.43 | 0.04 |
| 2 | — | 5,11,14-ester | 5,11,14-ester | 3.34 | 0.17 | 0.47 | 0.06 |
| 3 | — | 20:4n-6-ester | 20:4n-6-ester | 0.30 | 0.28 | 8.25 | 0.04 |
| 4 | — | 5,11,14-ester 20:4n-6-ester | 5,11,14-ester 20:4n-6-ester | 1.04 | 0.58 | 9.56 | 0.00 |
| 5 | Pre-incubation | 20:4n-6-ester | 20:4n-6-ester | 0.30 | 0.55 | 10.39 | 0.00 |
| 6 | 20:4n-6-ester | 5,11,14-ester | 5,11,14-ester | 2.12 | 0.38 | 5.30 | 0.03 |
| 7 | 20:4n-6-ester | Ethanol | Ethanol | 0.00 | 0.30 | 5.57 | 0.01 |
| 8 | 20:4n-6-ester | 20:4n-6-ester 5,11,14-ester | 20:4n-6-ester 5,11,14-ester | 0.98 | 1.05 | 12.90 | 0.01 |
| 9 | 20:4n-6-ester | 20:4n-6-ester + Ethanol | 20:4n-6-ester + Ethanol | 0.09 | 0.85 | 11.80 | 0.03 |

EXAMPLE 2
Effect of 5,11,14-eicosatrienoic Acid on the TNFα-section by Ultraviolet B Treated Human immortalized keratinocytes Immortalized human keratinocytes (DK2-NR) are incubated in culture plates (diameter 3.5 cm) with 1.5 ml NR-2 medium. After reaching confluency the $Ca^{2+}$-concentration in NR-2 medium is shifted to 1.5 mM. After 4 days, the cells are incubated 2×2 days in NR-2 without hydrocortisone, with a high concentration of $Ca^{2+}$ (1.5 mM) and various fatty acids (i.e. 18:2n-6, 18:3n-3, 20:3(5,11,14)). At the end of the incubation period the NR-2 medium is removed and stored at 37° C. to re-feed the cells after the UVB-treatment (conditioned NR-2 medium). The cell cultures are washed twice with HBSS. For the UVB-treatment the cells are incubated in 0.5 ml HBSS. The cell cultures are treated with 1.5 kJ UVB (Philips, TL100, maximum emission at 313 nm). Then, HBSS is replaced with the corresponding conditioned NR-2 medium. The supernatant is collected after 24 hours and is stored at −20° C. The secreted TNFα concentration in the supernatant is quantified by ELISA (Pelikine Compact, CLB Amsterdam, The Netherlands).

As listed in table 3 it could be shown that 5,11,14-eicosatrienoic acid inhibits the secretion of TNFα (9 pg/ml) in UVB-treated human immortalized keratinocytes compared to controls (11.6 pg/ml).

TABLE 3

| | Secreted TNFα [pg/ml] | ± SD |
|---|---|---|
| No UVB + control (EtOH) | 0.0 | 0 |
| UVB + control (EtOH) | 11.6 | 0.009 |
| UVB + 5,11,14 | 9.0 | 0.005 |
| UVB + 18:3n-3 (α-linolenic acid) | 14.5 | 0.015 |
| UVB + 18:1n-9 (oleic acid) | 12.1 | 0.005 |
| UVB + hydrocortisone (0.5 mg/ml) | 2.0 | 0.004 |

EXAMPLE 3
Anti-inflammatory Effect of Other NMIFAs

Determination of the anti-inflammatory effect of 18:3(5, 11,14), 18:3(3,9,12), 19:3(5,11,14), 19:3(4,10,13), 21:3(5, 11,14), 21:3(6,12,15), 22:3(5,11,14) and 22:3(7,13,16) in the human immortalized keratinocyte line DK2-NR (described in the patent PCT/EP96/05812) was achieved as described in Example 2 above. The results show that anti-inflammatory effects are exhibited.

EXAMPLE 4
Anti-inflammatory Activity of *Podocarpus nagi* Methyl Ester Following Topical Administration to the Mouse The anti-inflammatory activity of *Podocarpus nagi* methyl ester (containing 26% of C20:3 5,11,14; and containing 0.5% of α-tocopherol and 0.2% of ascorbyl palmitate) was evaluated in the arachidonic acid-induced aural oedema test in the mouse.

*Podocarpus nagi* methyl ester corresponds to the oil extracted from seeds of *Podocarpus nagi*, the extraction being carried out in accordance with the method described in the two paragraphs following Table 1 of the description.

The exact protocol is as follows: *Podocarpus nagi* methyl ester or the *Podocarpus nagi* control oil is administered topically to the right ear of mice at a concentration of 20% (4 micrograms in 20 microliters of acetone) once a day for 5 days. Each group contains 5 mice and one group receives only acetone. Arachidonic acid at a concentration of 2% in acetone is administered 1 hour after the final application of the treatments, and the thickness of the ear is measured with the aid of a micrometer (oditest) 1 hour after the administration of the arachidonic acid.

The *Podocarpus nagi* control oil corresponds to *Podocarpus nagi* methyl ester as described above in which the C20:3 5,11,14 has been essentially replaced by oleic acid (C18: 1n-9).
Results
The aural oedema corresponds to the increase in the thickness of the ear in relation to the group having received acetone only.

| Product administered topically | Aural oedema (mm $10^{-2}$) average ± mse | Inhibition of oedema (%) average ± mse | Student test (versus arachidonic acid group) |
|---|---|---|---|
| Arachidonic acid (AA) 2% | 11.75 ± 1.75 | — | — |
| Indomethacin 5% + AA | 1.00 ± 0.48 | 91.49 | $P < 0.001$ |
| *Podocarpus nagi* methyl ester + AA | 5.00 ± 0.95 | 57.45 | $P < 0.01$ |
| *Podocarpus nagi* oil + AA | 12.00 ± 2.10 | −2.13 | $P > 0.05$ (not significant) | mse: mean standard error

Indomethacin, a non-steroidal anti-inflammatory used as a positive control in the test at a concentration of 5% in acetone, greatly inhibits the oedema induced by arachidonic acid. *Podocarpus nagi* methyl ester at a concentration of 20% provides 57% inhibition of the arachidonic acid-induced oedema. These results show that *Podocarpus nagi* methyl ester exhibits an anti-inflammatory activity when it is administered topically to the skin of mice.

EXAMPLE 5
Analysis of the Lipids in the Skin Following Topical Administration of *Podocarpus nagi* Ethyl Ester to the Mouse

*Podocarpus nagi* ethyl ester corresponds to the oil extracted from seeds of *Podocarpus nagi*, the extraction being carried out in accordance with the method described in the two paragraphs following Table 1 of the description.

The exact protocol is as follows: *Podocarpus nagi* ethyl ester (with antioxidants) or the control mixture (with the same composition as *Podocarpus nagi* ethyl ester but in which the C20: 3 5,11,14 is essentially replaced by C18: 1n-9) is administered topically to the right ear of mice at a concentration of 20% (4 micrograms in 20 microliters of acetone) once a day for 5 days. Each group contains 4 mice. On the left ear, the mice receive only acetone. 2 hours after the final administration, the mice are sacrificed and biopsies are carried out on the ears thus treated for analysis of the cutaneous lipids.

The incorporation of C20: 3 5,11,14 into the phospholipids of the skin of the ear of mice was analysed as follows: Extraction of the lipids: 20 mg of each biopsy is extracted with 0.8 ml of $H_2O$, 1 ml of $CHCl_3$ and 2 ml of MeOH. Following centrifugation (3 minutes at 1000 g) the residue is re-extracted with 1 ml of $CHCl_3$, the supernatant is filtered through a glass frit and washed with 1 ml of 0.88% KCl. The organic phase is extracted and concentrated under nitrogen and redissolved in 2 ml of $CHCl_3$.

Separation of the phospholipids (PL) and the neutral lipids (NL): the different classes of lipids were separated by solid-phase chromatography on 3 ml columns containing 500 mg of silica (Supelco 57010). The samples as described above (in 2 ml of $CHCl_3$) were introduced into these washed columns. The NL were obtained with 2 ml of $CHCl_3$ and the PL with 4 ml of $CHCl_3$/MeOH (2/1) and 4 ml of MeOH. The samples are concentrated under nitrogen and redissolved in 10 ml of $CHCl_3$.

Thin-layer chromatography of the phospholipids: the samples of PL obtained above are introduced onto 10×10 thin-layer chromatography plates (Merck 1.13727) and the PL are separated in $CHCl_3$/MeOH/acetic acid/$H_2O$ (50/37.5/3.5/2.9). The PL are identified using reference samples.

Methylation of the phospholipids: the samples are subsequently methylated with 200 μl of methanolic HCl/hexane (4/1) containing 0.4 μg of C17:0 for 16 hours at 65° C. The reaction is subsequently neutralized with 0.5 ml of 6% $K_2CO_3$. The methyl esters (ME) are extracted twice with 300 μl of hexane, concentrated under nitrogen and redissolved in 5 μl of isooctane for analysis by gas chromatography.

Gas chromatography of the phospholipids: the ME are injected into the instrument Hewlett Packard GC Model 6890, equipped with a sample collector and a capillary column.

RESULTS: Fatty acids in the lipid pools after topical application of the ethyl esters of controls* (control) and ethyl esters of *Podocarpus nagi* (seed) on the mouse ear.

| Percentages Fatty acids | Composition of the ethyl esters administered topically | | Phospholipids | |
|---|---|---|---|---|
| | Control (+) | Seed (+*) | Control | Seed (+***) |
| c16:0 | 5.4 | 2.4 | 14.6 | 8.2 |
| c16:1n-7 | 0.3 | | 1.6 | 5.9 |
| c18:0 | 1.9 | 1.4 | 14.8 | 7.6 |
| c18:1n-9 | 43.9 | 16.4 | 20.0 | 15.5 |
| c18:2n-6 | 48.5 | 43.1 | 16.8 | 27.0 |
| c18:3n-3 | | | 0.0 | 0.3 |
| c20:2 5, 11 | | 0.4 | 0.0 | 0.2 |
| c20:3 5,11,14 | | 26.3 | 0.2 | 13.6 |
| c20:2n-6 | | 8.6 | 0.8 | 4.4 |
| c20:3n-6 | | | 0.7 | 0.2 |

-continued

| Percentages Fatty acids | Composition of the ethyl esters administered topically | | Phospholipids | |
|---|---|---|---|---|
| | Control (+) | Seed (+) | Control | Seed (+**) |
| c20:4n-6 | | | 9.9 | 2.2 |
| c20:5n-3 | 0.1 | | 0.3 | 0.0 |
| c23:0 | | | 0.3 | 0.0 |
| c22:2n-6 | | | 0.2 | 0.0 |
| c22:4n-6 | | | 1.1 | 0.0 |
| c22:5n-3 | | | 1.0 | 0.0 |
| c22:6n-3 | | | 9.3 | 1.0 |
| Σ(c12,c13,c14, c15:0) | | | 1.9 | 2.5 |
| Σ(c20, c22, c24, c26:0) | | | 4.4 | 9.7 |
| Σ(c20,c22,c24:1) | | 1.5 | 2.1 | 1.7 |
| Total | 100.0 | 100.0 | 100.0 | 100.0 |

*Saffron/sunflower/apricot (43/7/50)
**Antioxidants: 0.5% by weight α-tocopherol and 0.2% by weight ascorbyl palmitate The C20:3 5,11,14 increases in the phospho-lipids whereas the 20:4n-6 (arachidonic acid) decreases. These results show that C20:3 5,11,14 is incorporated into the skin phospholipids following topical application to the mouse.

The replacement of 20:4n-6 by C20:3 5,11,14 seems to correlate to the anti-inflammatory properties of C20:3 5,11, 14 evidenced after topical application in the model of arachidonic acid-induced aural oedema in the mouse (Example 4).

Example 6
Body Milk (Oil-in-water Emulsion)
Oily Phase:

| Glyceryl stearate/PEG-100 stearate (Arlacel 165 sold by ICI) (emulsifier) | 1% |
|---|---|
| Polysorbate 60 (emulsifier) | 0.8% |
| Hydrogenated polyisobutene | 2% |
| Stearic acid | 1% |
| Oil from seed of *Ephedra campylopoda* | 8% |

Aqueous Phase:

| Glycerin | 3% |
|---|---|
| Carbomer (carbopol 941 sold by Goodrich) (thickener) | 0.3% |
| Triethanolamine (neutralizing agent) | 0.3% |
| Preservative | 0.3% |
| Water | up to 100% |

The emulsion is prepared by incorporating the oily phase in the aqueous phase while stirring. The body milk provides good protection of the skin against inflammations.

EXAMPLE 7
Care Fluid (Oil-in-water Emulsion)
Oily Phase:

| Methylglucose sesquistearate (emulsifier) | 2% |
|---|---|
| Cyclomethicone | 13% |

-continued

| Oil from seed of *Podocarpus nagi* | 2% |
|---|---|
| Perfume | 0.2% |
| PEG 20 methylglucose sesquistearate (emulsifier) | 2% |

Aqueous Phase:

| Xanthan gum (thickener) | 0.2% |
|---|---|
| Polyacrylamide/isoparaffin $C_{13}$-$C_{14}$/laureth-7 (Sepigel 305 sold by Seppic) (thickener) | 0.8% |
| Preservative | 0.3% |
| Water | up to 100% |

The emulsion is prepared as describe in Example 6. A white fluid is obtained which provides good protection of the skin against inflammations.

Example 8
Care Cream (Water-in-oil Emulsion)
Oily Phase: (A)

| Polyglyceryl-4 Isostearate/cetyl dimethicone Copolyol/hexyl laurate (Abil WE 09 sold by Goldschmidt) (emulsifier) | 4% |
|---|---|
| Isohexadecane | 5% |
| Oil from seeds of *Caltha palustris* | 10% |
| Cyclomethicone | 3.5% |
| n-octanpyl-5-salicylic acid | 1% |
| Perfume | 0.15% |

Aqueous Phase: (B)

| Glycerin | 10% |
|---|---|
| Cellulose gum | 0.5% |
| Magnesium sulphate | 0.65% |
| Preservative | 0.3% |
| Water | up to 100% |

For preparing the emulsion, constituents of phase A are heated at 80° C. until completely dissolved, and are refrigerated at 65° C. Phase B is heated at 65° C., phase A is poured therein while stirring, then the mixture is refrigerated. A white fluid is obtained which provides good protection of the skin against inflammations.

What is claimed is:

1. A topical pharmaceutical or cosmetic composition comprising, as an active ingredient, at least one substance selected from the group consisting of non-methylene-interrupted fatty acids having formula (I), salts and esters thereof, along with a carrier for transporting the active ingredient into a superficial mammalian tissue,

wherein $R^1$ is a $C_1$–$C_5$ alkyl group and $R^2$ is a $C_2$–$C_6$ alkyl group.

2. A topical pharmaceutical or cosmetic composition according to claim 1, wherein $R^1$ is a $C_3$ alkyl group and $R^2$ is a $C_2$–$C_6$ alkyl group, or in which $R^2$ is a $C_4$ alkyl group and $R^1$ is a $C_1$–$C_5$ alkyl group.

3. A topical pharmaceutical or cosmetic composition according to claim 2, wherein the non-methylene-interrupted fatty acids are 20:3(5,11,14).

4. A topical pharmaceutical or cosmetic composition according to claim 1, wherein the non-methylene-interrupted fatty acids have been previously purified, synthesized, or are present in a mixture of fatty acids.

5. A pharmaceutical, food or cosmetic composition, comprising a combination of a fish oil and at least one substance selected from the group consisting of non-methylene-interrupted fatty acids of formula (I),

(I)

salts and esters thereof, wherein $R_1$ is a $C_1$–$C_5$ alkyl group and $R_2$ is a $C_2$–$C_6$ alkyl group.

6. A composition according to claim 1, further comprising liposoluble anti-oxidants.

7. A method to modulate the metabolism of lipids in superficial mammalian tissues comprising administering an effective amount of at least one substance selected from the group consisting of non-methylene-interrupted fatty acids of formula (I), salts and esters thereof to a mammal in need of such modulation,

(I)

wherein $R^1$ is a $C_1$–$C_5$ alkyl group and $R^2$ is a $C_2$–$C_6$ alkyl group.

8. A method to treat or prevent inflammation in superficial mammalian tissues comprising administering an effective amount of at least one substance selected from the group consisting of non-methylene-interrupted fatty acids of formula (I), salts and esters thereof to a mammal in need of such treatment of prevention,

(I)

wherein $R^1$ is a $C_1$–$C_5$ alkyl group and $R^2$ is a $C_2$–$C_6$ alkyl group.

9. A method according to claim 7, wherein the non-methylene-interrupted fatty acids are 20:3(5,11,14).

10. A method according to claim 8, wherein the non-methylene-interrupted fatty acids are 20:3(5,11,14).

11. A topical pharmaceutical or cosmetic composition according to claim 1, wherein the carrier is a liposome.

12. A topical pharmaceutical or cosmetic composition according to claim 1, further comprising a pharmaceutically or cosmetically acceptable vehicle.

13. The method of claim 7, wherein the at least one substance is administered along with a carrier for transporting the active ingredient into a superficial mammalian tissue.

14. The method of claim 8, wherein the at least one substance is administered along with a carrier for transporting the active ingredient into a superficial mammalian tissue.

15. The method of claim 13, wherein the carrier is a liposome.

16. The method of claim 14, wherein the carrier is a liposome.

17. The method of claim 7, wherein the at least one substance is administered along with a fish oil.

18. The method of claim 8, wherein the at least one substance is administered along with a fish oil.

19. The method of claim 13, wherein the carrier is a resistant starch.

20. The method of claim 14, wherein the carrier is a resistant starch.

21. A topical pharmaceutical or cosmetic composition according to claim 1, wherein the carrier is a resistant starch.

22. A topical pharmaceutical or cosmetic composition according to claim 1, further comprising a fish oil.

* * * * *